United States Patent [19]

Kanno et al.

[11] Patent Number: 5,223,434
[45] Date of Patent: Jun. 29, 1993

[54] APPARATUS AND METHOD FOR PRODUCING AND AUTOMATICALLY INJECTING $H_2{}^{15}O$

[75] Inventors: Iwao Kanno; Matsutaro Murakami, both of Akita; Yohjiro Toda; Tadasu Sugawara, both of Hokkaido; Masahiko Handa; Akira Mizuno, both of Tokyo, all of Japan

[73] Assignees: Kazuo Uemura, Atika; The Japan Steel Works, Ltd., Tokyo, both of Japan

[21] Appl. No.: 790,357

[22] Filed: Nov. 12, 1991

[51] Int. Cl.$^5$ ............ G01N 37/00; G01N 23/00
[52] U.S. Cl. .................. 436/56; 436/57; 436/813; 422/81; 422/963; 376/199; 250/363.03
[58] Field of Search ............ 436/56, 57, 813; 422/81, 903; 375/199; 250/363.03

[56] References Cited

U.S. PATENT DOCUMENTS

| | | | |
|---|---|---|---|
| 3,590,247 | 6/1971 | Holford | 250/83.3 |
| 4,148,608 | 4/1979 | Kaartinen | 23/230 PC |
| 4,812,775 | 3/1989 | Klinkowstein et al. | 328/233 |
| 4,910,149 | 3/1990 | Okube et al. | 436/57 |
| 5,032,728 | 7/1991 | Chang et al. | 250/363.4 |
| 5,082,980 | 1/1992 | Berridge | 568/917 |

FOREIGN PATENT DOCUMENTS

60-4900  1/1985  Japan .

OTHER PUBLICATIONS

Wieland et al., "Proton Accelerator Targets For The Production of Carbon-11, Nitrogen-13, Oxygen-15, and Fluorine-18", Chemical Abstracts, vol. 90, 1979, Abstract No. 90:194115T, p. 480, column R.
Clark et al., "Current Methodology For Oxygen-15 Production For Clinical Use", International Journal Of Radiation/Applications & Instrumentation Part A, vol. 38, No. 8, 1987, pp. 597–600.
Robinson et al., "A Series Target System For The Rapid, Sequential Production of water-150", Mol. Oxy. (15 02), and Molecular Fluorine (18 F2)' Chem. Abs., vol. 103, 1985, Abs. No. 103:130783P, Col. R.
World Patents Index Latest Derwent Publication Ltd., London, GB; AN 85-047008 and JP-A-60 004 900 (Sumimoto Heavy Ind) Jan. 11, 1985.

*Primary Examiner*—James C. Housel
*Assistant Examiner*—N. Bhat
*Attorney, Agent, or Firm*—Sughrue Mion Zinn Macpeak & Seas

[57] ABSTRACT

An apparatus for producing and automatically injecting $H_2{}^{15}O$, having: a target box adapted to be irradiated with a deuteron beam, a gas supplying device for supplying a hydrogen gas and a nitrogen gas as raw-material gases to the target box a radioactive-isotope conveying pipe connecting the target box and a vacuum pump for maintaining the interior of the target box and the interior of the radioactive-isotope conveying pipe in a vacuum state. In addition, the apparatus has an injection-fluid producing device and an automatic injection device, wherein the target box, the injection-fluid producing device and the automatic injection device are fluidly communicated with one another.

7 Claims, 8 Drawing Sheets

APPARATUS AND METHOD FOR PRODUCING AND AUTOMATICALLY INJECTING $H_2{}^{15}O$

BACKGROUND OF THE INVENTION

The present invention relates to a method of medical treatment using a radioactive isotope (RI), and more particularly to a production method and an injection device for using an RI having a short half life as an injection fluid.

With respect to a conventional system, the $^{15}O$ series has been introduced into a living body as an RI gas through an inhalation method. In this case, since the RI gas is inhaled through a mask, the RI gas can leak from the mask, so that the background and stability of a positron emission tomography (PET) apparatus may be impaired. In addition, with respect to the living body, since the RI gas is absorbed into blood vessels through the lungs, the period of inhalation becomes long, with the result that exposure.

Furthermore, since the aforementioned $^{15}O$ series RI gases have short half lives of only two minutes or thereabouts, in order to be taken in as a gas through the lungs as describe above, it is necessary to use a large amount of RI gas, thus increasing the operator's exposure.

In addition, in a case where an $H_2{}^{15}O$ gas is used as an injection fluid, a $^{15}O_2$ gas is heated by using platinum or palladium as a catalyst, and an $H_2$ gas is also made to pass through the catalyst when the $^{15}O_2$ gas passes through the catalyst, so as to synthesize $H_2{}^{15}O$. Then, a caponized compound is subjected to bubbling in physiological saline so as to produce an injection drug. However, since the half life is short, the efficiency has been poor.

SUMMARY OF THE INVENTION

The object of the present invention is to provide a safe and efficient method and an apparatus for rendering this method practical, thereby overcoming the above-described problems.

To attain the above-described objects, the subject invention provides the following 1) In an apparatus for producing $H_2{}^{15}O$, the following are provided: a target box 1 for irradiation with a deuteron beam; a gas supplying device 2 for supplying a hydrogen gas and a nitrogen gas serving as raw-material gases to the target box 1; and a vacuum pump 3 for maintaining the interior of the target box 1 and the interior of a RI conveying pipe 4 in a vacuum state.

2) In an injection-fluid producing device 5 the following are provided: an erected collecting bottle 51; an $H_2{}^{15}O$ introducing pipe which is open in a lower portion of a space in the collecting bottle 51 so as to cause bubbling by blowing $H_2{}^{15}O$, immediately after production thereof in the target box 1, into physiological saline filled in the collecting bottle 51; and an RI detector 56 for detecting a content of $H_2{}^{15}O$ contained in physiological saline in the collecting bottle 51.

3) In an automatic injection device 6, the following are provided: a syringe 66 for sucking an injection fluid produced in the collecting bottle 51, the syringe being adapted to send the injection fluid to an injection needle 64; three-way valves 61, 62, 65 for changing the direction of flow of the injection fluid to between the collecting bottle 51 and the syringe 66 and to between the syringe 66 and the injection needle 64; a bubble detector 68a disposed between the three-way valve 62 and the injection needle 64 and adapted to detect the presence of bubbles in the injection fluid immediately before the injection fluid is injected into a living body; a microporous filter 63 disposed between the three-way valve 62 and the injection needle 64; and a bubble detector 68 disposed in a pipe for sucking the injection fluid from the collecting bottle 51 and adapted to detect the presence or absence of bubbles.

4) The amount of RI in an injection fluid is detected by providing physiological saline in a collecting bottle; introducing $H_2{}^{15}O$ produced through nuclear reaction into the physiological saline and absorbing the $H_2{}^{15}O$ into the physiological saline; and detecting whether a content of $H_2{}^{15}O$ contained in the physiological saline is reached a predetermined radiation amount by means of a radioactive isotope detector.

5) Bubble detection is conducted by the bubble detector 68 in a pipe for sucking and conveying the injection fluid synthesized in the collecting bottle 51, by means of the syringe 66, and if bubbles are detected by the bubble detector 68a immediately before injection, the operation of the syringe 66 is stopped.

As described above, it is possible to produce an injection fluid of a required amount immediately before injection and to execute the injection immediately. In addition, it is possible to cause the injection fluid to reach an affected part of a living body directly through blood vessels. Accordingly, the period of diagnosis can be reduced as compared with a conventional gas inhalation method.

BRIEF DESCRIPTION OF THE DRAWINGS

FIG. 3(1)–3(7) are a diagram illustrating the state of operation in step 2–8 in the injection-fluid producing device and the automatic injection device;

FIG. 3(2) illustrates the state of operation in step 3 in the injection-fluid producing device and the automatic injection device;

FIG. 3(3) illustrates the state of operation in step 4 in the injection-fluid producing device and the automatic injection device;

FIG. 3(4) illustrates the state of operation in step 5 in the injection-fluid producing device and the automatic injection device;

FIG. 3(5) illustrates the state of operation in step 6 in the injection-fluid producing device and the automatic injection device;

FIG. 3(6) illustrates the state of operation in step 7 in the injection-fluid producing device and the automatic injection device;

FIG. 3(7) illustrates the state of operation in step 8 in the injection-fluid producing device and the automatic injection device;

FIG. 5(4)–5(4) are diagrams illustrating the state of operation of a sampling steps.

DETAILED DESCRIPTION OF THE PREFERRED EMBODIMENTS

Figure 1:
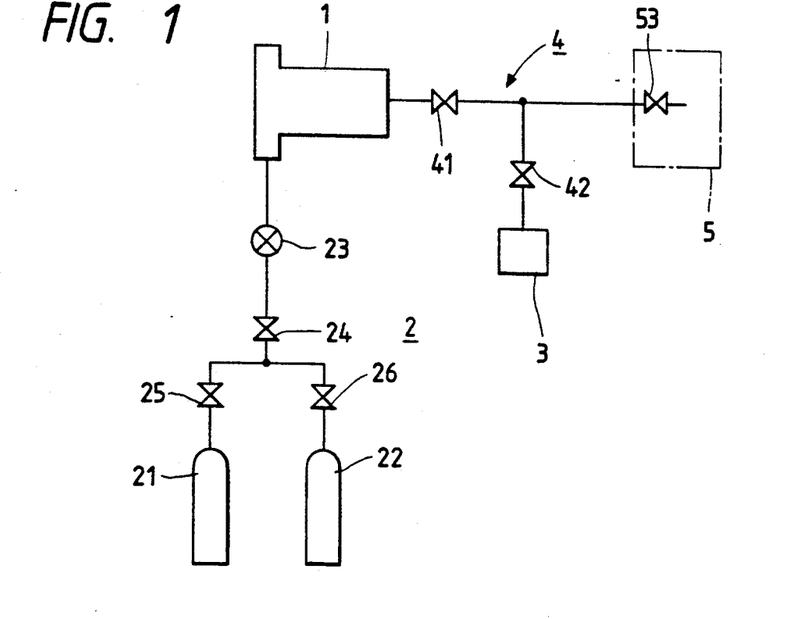
FIG. 1 is a schematic diagram of an apparatus for producing $H_2{}^{15}O$.

First, a description will be given of a method of producing $H_2{}^{15}O$ and an apparatus thereof. FIG. 1 is a schematic diagram of an apparatus for producing $H_2{}^{15}O$. This apparatus comprises a target box 1, a gas supplying device 2, an RI conveying pipe 4, and a vacuum pump 3 for reducing the pressure within the target box 1 and the RI conveying pipe 4.

The gas supplying device 2 includes a raw-material gas cylinder 21 in which $H_2$ and $N_2$ are mixed, a conveying gas cylinder 22 containing He gas, a pressure-regulating valve 23 and a solenoid valve 24 that is disposed midway in a pipe leading from the gas cylinders 21, 22 to the target box 1, a solenoid valve 25 disposed at an outlet of the raw-material gas cylinder 21, and a solenoid valve 26 disposed at an outlet of the conveying gas cylinder 22.

A solenoid valve 41 is disposed in the RI conveying pipe 4 at an outlet of the target box 1, and after the portion of the RI conveying pipe 4 downstream of this solenoid valve 41 is branched off, the vacuum pump 3 is connected thereto via a solenoid valve 42. Furthermore, a pipe is provided between the branching point and a solenoid valve 53 of an injection-fluid producing device 5.

Since the RI gas having radioactivity passes through the interior of the RI conveying pipe 4, the exterior thereof is provided with shielding against radioactivity.

A description will now be given of the action (including a method of operation) of the above-described apparatus for producing $H_2{}^{15}O$.

First, the solenoid valves 25, 26 and the solenoid valve 53 provided in the injection-fluid producing device 5 are closed, the interior of the target box 1 and the interior of the RI conveying pipe 4 and the like are set in a vacuum state by means of the vacuum pump 3, and cleaning is carried ont.

Then, the solenoid valve 42 is closed, the solenoid valve 25 is opened, and the raw-material gas is filled in the target box 1 and the RI conveying pipe 4.

Subsequently, the above-described cleaning and filling of the raw-material gas are repeated a number of times so as to effect cleaning sufficiently.

After the above cleaning step is accomplished, the solenoid valve 41 is closed, the raw-material gas which is regulated in a predetermined pressure by the pressure-regulating valve 23 is filled in the target box 1, the solenoid valve 24 is closed, and the operation is set in a standby state.

The raw-material gas in the target box 1 is irradiated with a deuteron beam generated by a cyclotron at a required timing.

Through this irradiation, the raw-material gas undergoes the following nuclear reaction so that $H_2{}^{15}O$ is produced. That is, $$^{14}N_2 \xrightarrow{(d, n)} {}^{15}O \xrightarrow{H_2} H_2^{15}O$$

After irradiation, the solenoid valve 53 is opened, and $H_2{}^{15}O$ thus produced is conveyed at a stroke to the injection-fluid producing device 5. In this case, $H_2{}^{15}O$ remaining in the target box 1 is conveyed completely to the injection-fluid producing device 5 by means of the helium gas in the conveying gas cylinder 22.

A description will now be given of the injection-fluid producing device 5.

Figure 2:
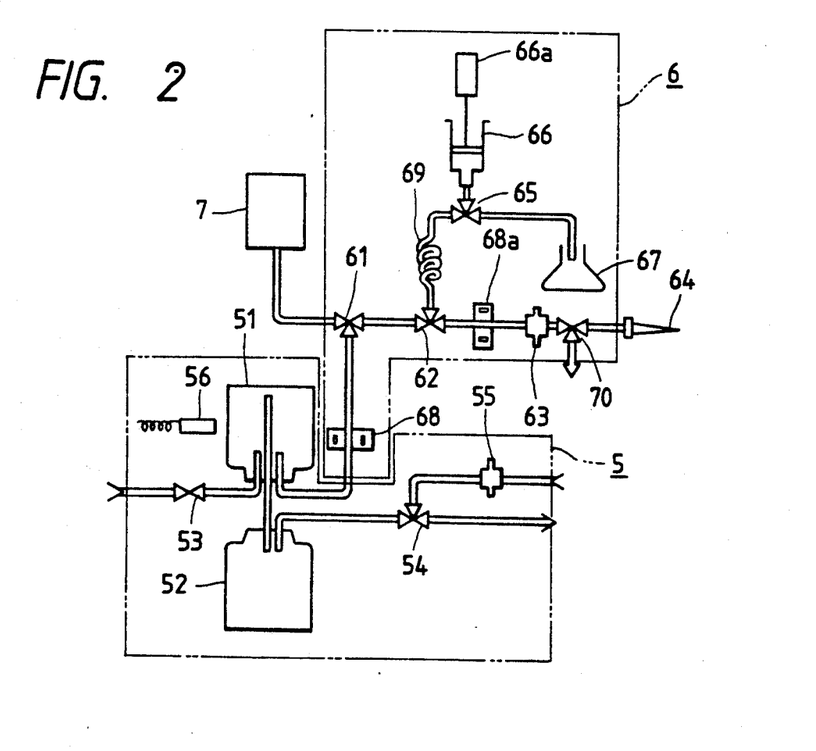
FIG. 2 is a schematic diagram of an injection-fluid producing device and an automatic injection device.
Figure 3:
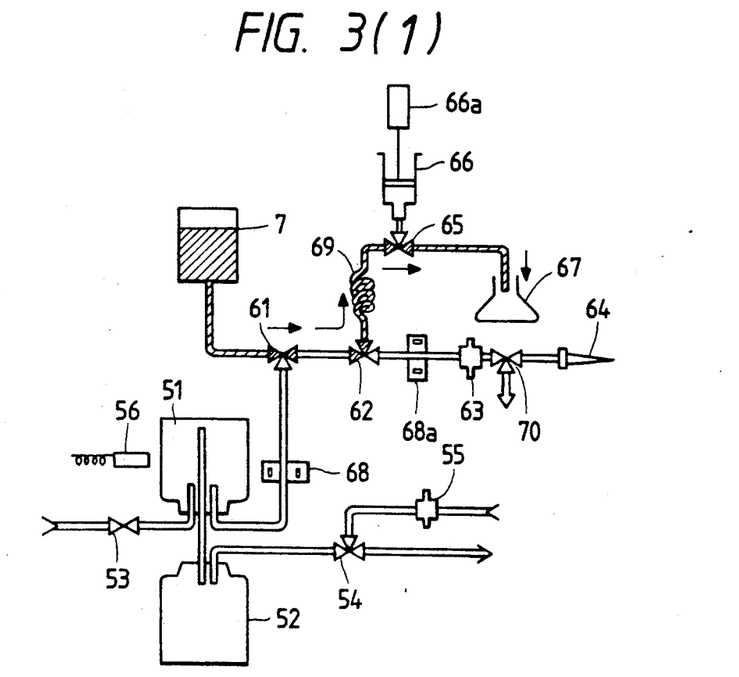

This device is enclosed by a dotted-chain line in FIG. 2, and a collecting bottle 51 which is inversely erected and a fluid accumulating bottle 52 which is normally erected are fluidly communicated with each other by means of a capillary tube in such a manner as to connect together an upper space in the collecting bottle 51 and an upper space in the fluid accumulating bottle 52 by penetrating their caps.

In addition, the pipe connected to the RI conveying pipe 4 through the solenoid valve 53 penetrates the cap of the collecting bottle 51 and is open in a lower space of its interior. Further, a pipe for penetrating the cap of the collecting bottle 51 and communicating the lower space of the collecting bottle 51 with an automatic injection device 6 is provided so as to send the injection-fluid to the automatic injection device 6.

Meanwhile, in addition to the pipe leading from the collecting bottle 51 and penetrating the cap of the fluid accumulating bottle 52, a pipe connected to a three-way valve 54 is provided to the fluid accumulating bottle 52. A microporous filter 55 is connected to one of the other two ports of this three-way valve 54 and is arranged to take in the room air, while the other is arranged to discharge an exhaust gas.

Furthermore, an RI detector 56 is provided in proximity to the collecting bottle 51.

Meanwhile, the automatic injection device 6 is also enclosed by a two-dotted chain line in FIG. 2, and is connected to a three-way valve 61 by means of pipe leading from the lower portion of the space in the collecting bottle 51 and penetrating its cap. A three-way valve 62 is connected to one of the other two ports of the three-way valve 61, and a injection needle 64 is connected to this port of the three-way valve via a microporous filter 63.

In addition, a three-way valve 65 is connected to one of the other ports of the three-way valve 62, and a syringe 66 is connected to one of the other ports of the three-way valve 65, while a pipe leading to a waste fluid bottle 67 is connected to still another port thereof.

Furthermore, a bubble detector 68 is provided to the pipe between the three-way valve 61 and the collecting bottle 51, while a bubble detector 68a is provided to the pipe between the three-way valve 62 and the microporous filter 63.

It should be noted that an external physiological saline tank 7 is connected to one of the ports of the three-way valve 61.

A description will now be given of the action (operation) of the injection-fluid producing device 5 and the automatic injection device 6.

Disposable parts are used for all the bottles 51, 52, 67, the syringe 66, the injection needle 64, the microporous filter 63, and the three-way valves 61, 62, 65 that are used for the above-described injection-fluid producing device 5 and automatic injection device 6, as well as all the other than the $H_2{}^{15}O$ introducing that are in contact with the injection fluid.

Figure 4:
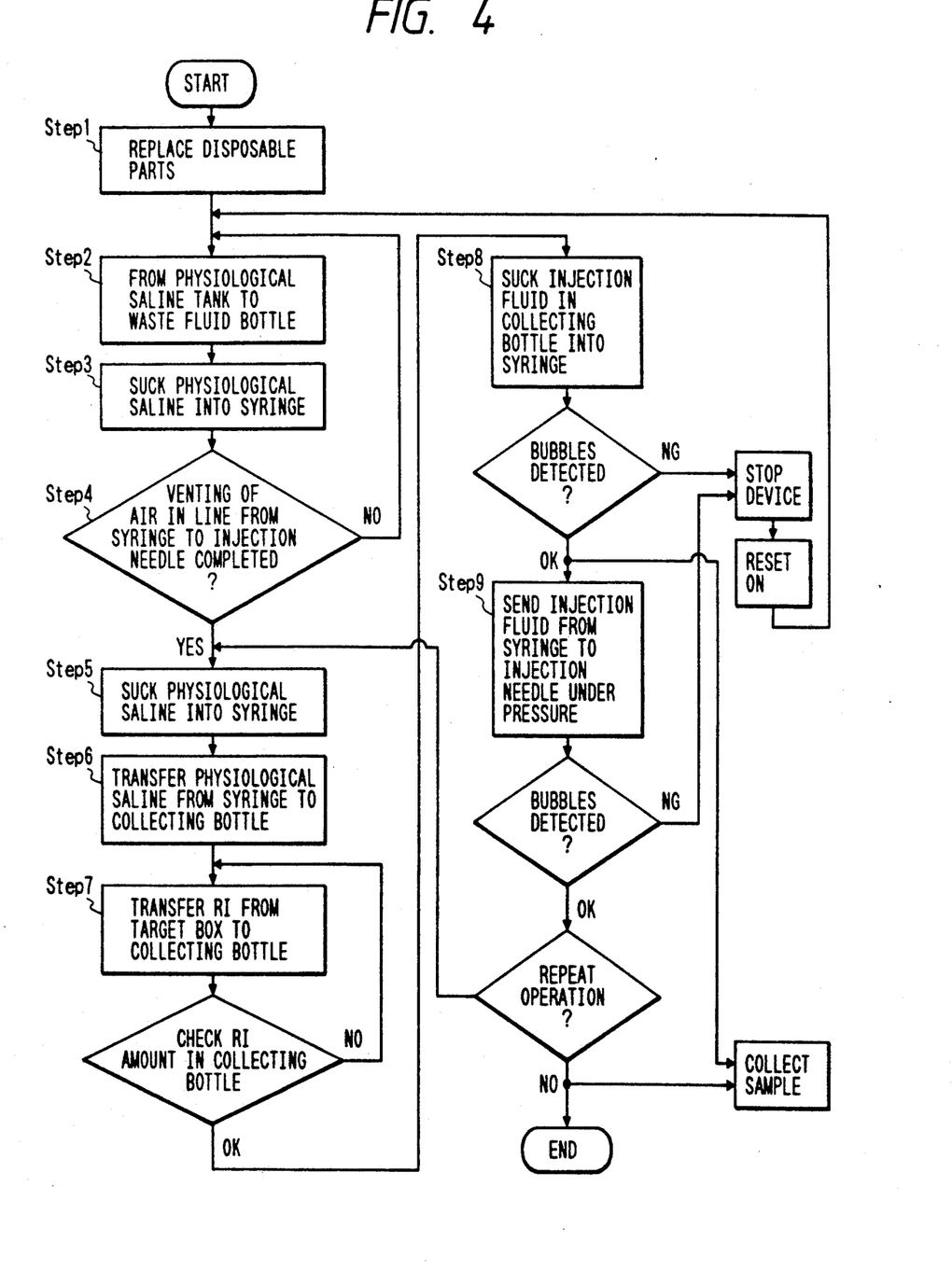
FIG. 4 is a flowchart of each step.
Figure 5:
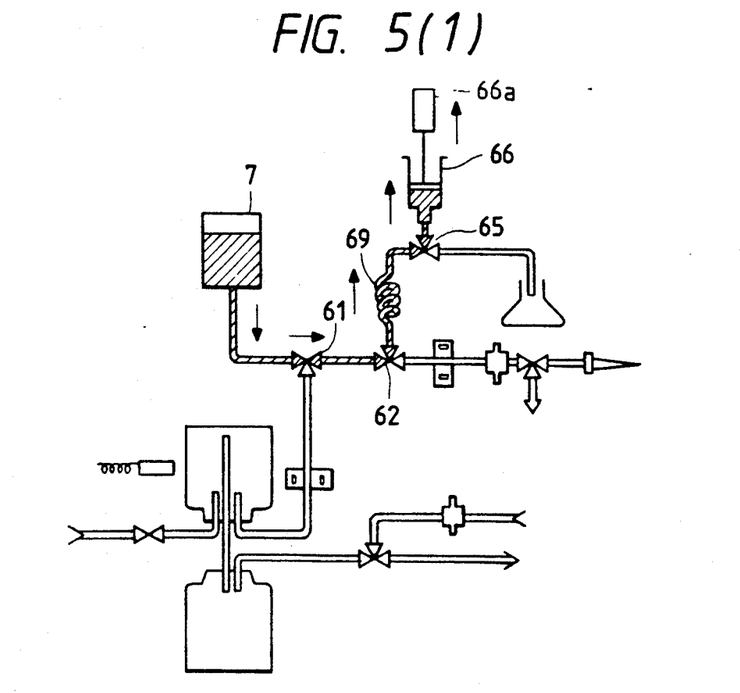

FIGS. 3(1)–3(8) the action of each operation (step) of the injection-fluid producing device 5 and the automatic injection device 6, and FIG. 4 is a flowchart of the steps.

Each action (operation) will be described with reference to this flowchart.

Step 1: All the disposable parts are replaced with new ones. These disposable parts include the collecting bottle 51, the fluid accumulating bottle 52, the physiological saline tank 7, the three-way valves 61, 62, 65, the syringe 66, the waste fluid bottle 67, the microporous filter 63, the injection needle 64, and the pipes connecting the respective adjacent members.

Step 2: FIG. 3(1) The physiological saline is allowed to fall by its own weight and to flow from the physiological saline tank 7 to the waste fluid bottle 67 so as to vent the air existing therebetween. This state is shown by a darkened portion in FIG. 3(1). Hereinafter, the portions where the gas and fluid flows in each step are indicated by darkened portions.

Step 3: (FIG. 3(2) Physiological saline is sucked into the syringe 66 from the physiological saline tank 7 via the three-way valve 61, 62, 65 by means of a syringe driving device 66a.

Step 4: FIG. 3(3) The physiological saline sucked in Step 3 is allowed to flow from the syringe 66 to the injection needle 64 via the three-way valves 65 and 62 so as to vent the air existing therebetween by means of the syringe driving device 66a.

In this case, it is possible to completely vent the air by repeating Steps 1 to 4 any number of times.

Step 5: FIG. 3(4) The physiological saline is allowed to flow from the physiological saline tank 7 via the three-way valves 61, 62, 65 so as to be sucked by the syringe 66.

Step 6: FIG. 3(5) The physiological saline sucked in Step 5 is allowed to flow via the three-way valves 65, 62, 61 so as to be transferred to the collecting bottle 51.

Step 7: FIG. 3(6) $H_2{}^{15}O$ together with the conveying gas is sent from the target box 1 to the collecting bottle 51 via the RI conveying pipe 4 and the solenoid valve 53.

The conveying gas other than $H_2{}^{15}O$ absorbed in the collecting bottle 51 is accumulated in a waste gas cylinder via the fluid accumulating bottle 52 and the three-way valve 54.

While $H_2{}^{15}O$ together with the conveying gas is being sent, the RI detector detects the amount of $H_2{}^{15}O$ absorbed, and Step 7 is continued until a predetermined amount is reached. When the predetermined amount is reached and a predetermined injection fluid is obtained, the operation proceeds to Step 8.

Step 8: (FIG. 3(7) The injection fluid in the collecting bottle 51 is sucked by the syringe 66 in such a manner that $H_2{}^{15}O$ is accumulated in a coil portion 69 of the pipe via the three-way valves 61, 62, 65.

In this case, since the pipe provided between the collecting bottle 51 and the three-way valve 61 is so arranged that the injection fluid passes through the photoelectric-type bubble detector 68, the presence or absence of bubbles in the injection fluid being sent is detected. If the bubbles are not detected, the operation proceeds to Step 9, and if they are detected, the sucking operation of the syringe 66 is stopped.

In addition, when the injection fluid in the collecting bottle 51 is sucked by the syringe 66, air in the room flows into the collecting bottle 51 via the microporous filter 55, the three-way valve 54, and the fluid accumulating bottle 52 so as to prevent the pressure within the collecting bottle 51 from being reduced.

Step 9: FIG. 3(8) $H_2{}^{15}O$ accumulated in the coil portion 69 is allowed to reach the injection needle 64 via the three-way valve 65, 62 and the microporous filter 63 by means of the injection fluid sucked by the syringe 66, so as to be injected into the living body. In this case, a check is made by the bubble detector 68a for detecting the presence or absence of bubbles.

In this case, since the operation is usually repeated a number of times in clinical diagnosis using $H_2{}^{15}O$, air venting can be omitted, and the operation, starting with Step 5, can be repeated to reduce time.

A series of operations is completed when the administration of a number of injections is completed.

It should be noted that, after completion of administration to the living body or prior to the administration, as shown in diagrams explaining sampling steps shown in FIG. 5(1)–5(4) sampling can be effected as shown below, and an inspection for administration to a living body can be conducted.

(1) Physiological saline is sucked into the syringe 66 (FIG. 5(1).

(2) The physiological saline is allowed to enter the collecting bottle 51 (FIG. 5(2).

(3) The physiological saline is sucked into the syringe 66 from the collecting bottle 51 (FIG. 5(3).

(4) If a three-way valve 70 is interposed between the microporous filter 63 and the injection needle 64, it is possible to obtain a sample by changing over the three-way valve 70 without removing the injection needle 64.

Needless to say, by pressing a button for sampling, the aforementioned Steps (1) to (4) can be automatically operated.

With respect to the above-described steps, the changeover of the solenoid valve 53 and the three-way valves 54, 61, 62, 65 and the vertical movement of the syringe 66 can be automatically effected simply by pressing an operation button of an unillustrated controller.

In addition, if bubbles are present in the injection fluid, an injection into the living body cannot be effected under any circumstance. Accordingly, at the time when the injection fluid is sucked into the syringe 66 from the collecting bottle 51, the presence or absence of bubbles is detected by the photoelectric-type bubble detector 68, and if the bubbles are present, the sucking operation of the syringe 66 is stopped.

In Step 9, at the time of executing an injection, the presence or absence of bubbles is checked by the bubble detector 68a, and if the bubbles are present, the injecting operation of the syringe 66 is stopped. In the case where the just-mentioned operation has occurred, a reset is made and the operation is repeated with Step 1. In addition, as for the injection fluid, air trapping and sundry bacteria processing are conducted by means of the microporous filter 63 located downstream of the injection needle 64.

Furthermore, since the speed of injection by means of the syringe 66 is made variable, it is possible to execute an injection at a speed corresponding to the state of the living body.

It should be noted that since the $^{15}O$ series has a half life of two minutes or thereabouts, the arrangement provided is such that, in order to fix the injection period, the timer of the controller is started to count down after sucking the injection fluid into the syringe 66 in Step 8, thereby prompting the operator to execute an injection. This timer is so arranged that settings can be made variably depending on conditions.

As described above, since it is possible to automatically inject an RI into the living body speedily and under a clean condition, the following advantages can be obtained:

1) Because of speediness, it does not take much time, and it is unnecessary to produce an RI in large quantities by a cyclotron.

2) Since the RI is not produced in large quantities, and an injection can be effected automatically, exposure of the operator can be reduced to a remarkable degree.

3) Since an injection into a living body is effected directly, the period until the RI reaches the affected site via blood vessels can be reduced, and the period of diagnosis can therefore be reduced. In addition, since exposure of the living body is alleviated substantially, although diagnosis using a $^{15}O$ series gas has up until now been possible only once, diagnosis can be conducted a number of times, so that the reliability of diagnosis of such as malignant tumors can be enhanced.

4) Since the detection of bubbles in the injection fluid is carried out at two points, the operator can be assured that no bubbles will be injected into the patient.

5) By incorporating a sampling step, it is possible to inspect the drug administered ($H_2^{15}O$) at any time during an operation.

What is claimed is:

1. An apparatus for producing $H_2^{15}O$, comprising:
   a target box adapted to be irradiated with a deuteron beam;
   means connected to said target box for supplying a hydrogen gas and a nitrogen gas as raw-material gases to said target box; and
   means for irradiating said hydrogen gas and said nitrogen gas with a deuteron beam so as to produce $H_2^{15}O$; and
   a radioactive-isotope conveying pipe connected to said target box; and
   a vacuum pump connected to said target box and said radioactive-isotope conveying pipe for maintaining the interior of said target box and the interior of said radioactive-isotope conveying pipe in a vacuum state.

2. An apparatus as claimed in claim 1, further comprising:
   a collecting bottle connected to said radioactive isotope conveying pipe;
   an $H_2^{15}O$ introducing pipe in communication with a lower space of said collecting bottle and said radioactive isotope conveying pipe so as to allow said $H_2^{15}O$ to be introduced into physiological saline disposed in said collecting bottle; and
   a radioactive isotope detector in operative association with said collecting bottle for detecting a content of $H_2^{15}O$ contained in the physiological saline in said collecting bottle.

3. An injection-fluid producing device comprising:
   a collecting bottle;
   an $H_2^{15}O$ introducing pipe in communication with a lower space of said collecting bottle and said radioactive isotope conveying pipe in order to cause bubbling by blowing $H_2^{15}O$ into physiological saline disposed in said collecting bottle; and
   a radioactive isotope detector in operative association with said collecting bottle for detecting a content of $H_2^{15}O$ contained in the physiological saline in said collecting bottle said injection fluid comprises the physiological saline having $H_2^{15}O$ therein.

4. An apparatus as claimed in claim 3, further comprising:
   an injection needle;
   a syringe coupled to said collecting bottle and said injection needle for drawing the injection fluid from said collecting bottle and sending the injection fluid to said injection needle;
   a plurality of three-way valves provided between said collecting bottle and said syringe and between said syringe and said injection needle for changing the direction of flow of the injection fluid;
   a filter disposed between one of said three-way valves and said injection needle;
   a pipe connecting said collecting bottle with said syringe;
   a first bubble detector adapted to detect the presence or absence of bubbles in said pipe when the injection fluid is drawn from said collecting bottle; and
   a second bubble detector adapted to detect the presence or absence of bubble in the injection fluid immediately before the injection fluid passes through said injection needle.

5. A device for automatically injecting an injection fluid collected in a collecting bottle, comprising:
   an injection needle;
   a syringe coupled to said collecting bottle and said injection needle for sucking the injection fluid from said collecting bottle and sending the injection fluid to said injection needle;
   a plurality of three-way valves provided between said collecting bottle and said syringe and between said syringe and said injection needle for changing the direction of flow of the injection fluid;
   a microporous filter disposed between one of said three-way valves and said injection needle;
   a pipe connecting said collecting bottle with said syringe;
   a first bubble detector adapted to detect the presence or absence of bubbles in said pipe when the injection fluid is sucked from said collecting bottle; and
   a second bubble detector adapted to detect the presence or absence of bubbles in the injection fluid immediately before the injection fluid passes through said injection needle.

6. A method of detecting an amount of a radioactive isotope in an injection fluid, comprising the steps of:
   providing physiological saline in a collecting bottle;
   introducing $H_2^{15}O$ produced through nuclear reaction into said physiological saline and absorbing said $H_2^{15}O$ into said physiological saline; and
   detecting whether an amount of $H_2^{15}O$ contained in said physiological saline has reached a predetermined radiation amount with a radioactive isotope detector.

7. A method of detecting the presence or absence of bubbles in an injection fluid, comprising the steps of:
   detecting bubbles in a first pipe, connected to a syringe for sucking and conveying an injection fluid synthesized in a collecting bottle, with a first bubble detector;
   detecting bubbles in a second pipe, located immediately before an injection needle, with a second bubble detector; and
   stopping the operation of said syringe in the case where bubbles are detected by at least one of said first bubble detector and said second bubble detector.

* * * * *